United States Patent
Asmus et al.

(10) Patent No.: US 10,557,055 B2
(45) Date of Patent: Feb. 11, 2020

(54) CONFORMABLE COATING COMPOSITION COMPRISING FLUORINATED COPOLYMER

(71) Applicant: 3M INNOVATIVE PROPERTIES COMPANY, St. Paul, MN (US)

(72) Inventors: Robert A. Asmus, Hudson, WI (US); Hae-Seung Lee, Woodbury, MN (US); Dong-Wei Zhu, North Oaks, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 198 days.

(21) Appl. No.: 15/325,765

(22) PCT Filed: Jul. 2, 2015

(86) PCT No.: PCT/US2015/038969
§ 371 (c)(1),
(2) Date: Jan. 12, 2017

(87) PCT Pub. No.: WO2016/010742
PCT Pub. Date: Jan. 21, 2016

(65) Prior Publication Data
US 2017/0145248 A1      May 25, 2017

Related U.S. Application Data

(60) Provisional application No. 62/024,043, filed on Jul. 14, 2014.

(51) Int. Cl.
| | |
|---|---|
| *A61K 9/70* | (2006.01) |
| *C09D 133/16* | (2006.01) |
| *A61L 26/00* | (2006.01) |
| *C08F 220/18* | (2006.01) |
| *C08F 230/08* | (2006.01) |
| *C09D 143/04* | (2006.01) |

(52) U.S. Cl.
CPC ........ *C09D 133/16* (2013.01); *A61L 26/0014* (2013.01); *C08F 220/18* (2013.01); *C08F 230/08* (2013.01); *C09D 143/04* (2013.01); *C08F 2220/1825* (2013.01)

(58) Field of Classification Search
None
See application file for complete search history.

(56) References Cited

U.S. PATENT DOCUMENTS

| | | | |
|---|---|---|---|
| 3,786,116 A | 9/1974 | Delahunty | |
| 3,836,377 A | 9/1974 | Delahunty | |
| 3,842,059 A | 10/1974 | Milkovich | |
| 4,182,823 A | 1/1980 | Schoenberg | |
| 4,365,049 A | 12/1982 | Tsunoda | |
| 4,565,883 A | 1/1986 | Sieger | |
| 4,650,826 A | 3/1987 | Waniczek | |
| 4,732,808 A | 3/1988 | Krampe | |
| 4,972,037 A | 11/1990 | Garbe | |
| 4,981,902 A | 1/1991 | Mitra | |
| 5,061,481 A | 10/1991 | Suzuki | |
| 5,103,812 A | 4/1992 | Salamone | |
| 5,209,924 A | 5/1993 | Garbe | |
| 5,229,435 A | 7/1993 | Sakai | |
| 5,665,337 A | 9/1997 | Carballada | |
| 5,667,771 A | 9/1997 | Carballada | |
| 5,981,621 A | 11/1999 | Clark | |
| 6,183,593 B1 | 2/2001 | Narang | |
| 6,264,934 B1 | 7/2001 | Kantner | |
| 2007/0054133 A1 | 3/2007 | Sherman | |
| 2008/0143003 A1 | 6/2008 | Phelan | |
| 2011/0118403 A1 | 5/2011 | Wood | |
| 2011/0166492 A1 | 7/2011 | Holm | |
| 2012/0083568 A1 | 4/2012 | Soucek | |
| 2012/0276041 A1 | 11/2012 | Salamone | |
| 2013/0224373 A1 | 8/2013 | Jariwala | |
| 2013/0303654 A1 | 11/2013 | Salamone | |
| 2014/0303312 A1* | 10/2014 | Tomko | C08F 220/18 524/544 |

FOREIGN PATENT DOCUMENTS

| | | |
|---|---|---|
| CN | 101544868 | 9/2009 |
| JP | 2856932 | 12/1992 |
| WO | WO 2015-138175 | 9/2015 |

OTHER PUBLICATIONS

ShinEtsu : Silicone Fluids : Modified Silicone Fluids; Product Information Sheet, retrieved by internet on Mar. 26, 2014 [http://www.silicone.jp/e/products/type/oil/detail/search/deg07.shtml], 1 page.
Kawakami, "Silicone Macromers for graft polymer Synthesis", Polymer Journal, 1982, vol. 14, No. 11, pp. 913-917.
Kawakami, "Synthesis and Copolymerization of polysiloxane macromers", Division of Polymer chemistry, Inc., ACS Polymer Preprints, 1984, vol. 25, No. 1, pp. 245-246.
International Search report for PCT International application No. PCT/US2015/038969 dated Aug. 26, 2015, 5 pages.

* cited by examiner

*Primary Examiner* — Susan T Tran
(74) *Attorney, Agent, or Firm* — Ashley M. Dreis

(57) ABSTRACT

Conformable coating composition are described comprising a (meth)acrylate copolymer comprising interpolymerized monomer units of fluorinated monomer and a volatile solvent having a solubility parameter from 4.9-12.5 (cal/cm³)^{1/2}. In some embodiments, the fluorinated monomer has a Tg <30° C. In some embodiments, the dried coating exhibits no blocking and no greater than 75% failure at an elongation of 100%. Also described is a conformable film comprising a dried coating composition of the coating compositions described herein, articles comprising a layer of the conformable film on a substrate, and a copolymer comprising interpolymerized units of fluorinated monomer(s), silane monomer(s); and one or more monomers having a Tg ≥50° C.

9 Claims, No Drawings

CONFORMABLE COATING COMPOSITION COMPRISING FLUORINATED COPOLYMER

CROSS REFERENCE TO RELATED APPLICATIONS

This application is a national stage filing under 35 U.S.C. 371 of PCT/US2015/038969, filed Jul. 2, 2015, which claims the benefit of U.S. Provisional Application No. 62/024,043, filed Jul. 14, 2014, the disclosures of which are incorporated by reference in their entirety herein.

FIELD

The present disclosure relates to a conformable coating composition that comprises a copolymer and a solvent, and coatings therefrom that are useful as barrier films in medical applications.

SUMMARY

Although various conformable coating compositions have been described that are suitable for use as liquid bandages, industry would find advantage compositions having improved properties, such as reduced blocking of the dried coating and/or reduced failure when the dried coating is elongated.

In one embodiment, a conformable coating composition is described comprising a (meth)acrylate copolymer comprising interpolymerized monomer units of fluorinated monomer having a Tg <30° C. and a volatile solvent having a solubility parameter from 4.9-12.5 (cal/cm$^3$)$^{1/2}$. In some embodiments, the fluorinated monomer has a Tg <20° C. or <10° C. or <0° C. In some embodiments, the fluorinated monomer comprises a fluoroalkyl group and an acrylate group.

In another embodiment a conformable coating composition comprising a (meth)acrylate copolymer comprising interpolymerized monomer units of a i) at least one fluorinated monomer, ii) at least one monomer having a Tg ≥20° C., iii) a silane monomer having a Tg <10° C.; and a volatile solvent having a solubility parameter from 4.9-12.5 (cal/cm$^3$)$^{1/2}$. The dried coating exhibits no blocking and no greater than 75% failure at an elongation of 100%.

Also described is a conformable film comprising a dried coating composition of the coating compositions described herein; as well as articles comprising a layer of the conformable film on a substrate.

Also described is a copolymer having the general formula:

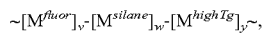

wherein
v is 5 to 60 wt-% of one or more fluorinated monomers having a Tg <20° C.;
w is 15 to 90 wt-% of one or more silane monomers; and
y is 15 to 80 wt-% of one or more monomers having a Tg ≥50° C.

DETAILED DESCRIPTION

"Alkyl" means a linear or branched, cyclic or acrylic, saturated monovalent hydrocarbon, e.g., methyl, ethyl, 1-propyl, 2-propyl, pentyl, dodecyl and the like.
"Alkylene" means a linear or a branched divalent saturated hydrocarbons, e.g., methylene, ethylene, propylene, 2-methylpropylene, pentylene, hexylene, dodecylene and the like.

"Aryl" means a monovalent aromatic, such as phenyl, naphthyl and the like.
"Arylene" means a polyvalent, aromatic, such as phenylene, naphthalene, and the like.
As used herein, "(hetero)hydrocarbyl" is inclusive of hydrocarbyl alkyl and aryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

The conformable coating composition comprises a (meth)acrylate copolymer. The (meth)acrylate copolymer comprises interpolymerized monomer units of at least one fluorinated monomer, [M$^{fluor}$].

The fluorinated monomer typically comprises a fluoroalkyl or perfluoroalkyl group. The term "fluoroalkyl group" refers to alkyl groups in which some or all C—H bonds are replaced by C—F bonds. The term "perfluoroalkyl group" includes alkyl groups in which all C—H bonds are replaced by C—F bonds as well as groups having one hydrogen present in place of a terminal fluorine atom. In some embodiments of perfluoroalkyl groups, when at least one hydrogen is present, the perfluoroalkyl group includes at least one difluoromethyl group. Suitable perfluoroalkyl groups comprise 2 to 12 (i.e. 2, 3, 4, 5, 6, 7, 8, 9, 10, 11, or 12) carbon atoms.

In some embodiments, the perfluoroalkyl group comprises 3 to 6 carbon atoms such as in the case of perfluoro-n-hexyl, perfluoro-n-pentyl, perfluoroisopentyl, perfluoro-n-butyl, perfluoroisobutyl, perfluoro-sec-butyl, perfluoro-tert-butyl, perfluoro-n-propyl, or perfluoroisopropyl).

Suitable fluorinated monomers include for example 2,2,2-trifluoroethyl (meth)acrylate; 2,2,3,3,3-pentafluoropropyl (meth)acrylate; 2,2,3,3,4,4,4-heptafluorobutyl (meth)acrylate; 2,2,3,3,4,4,5,5,5-nonafluoropentyl (meth)acrylate; 2,2,3,3,4,4,5,5,6,6,6-undecafluorohexyl (meth)acrylate; 2,2,3,3,4,4,5,5,6,6,7,7,7-tridecafluoroheptyl (meth)acrylate; 2,2,3,3,4,4,5,5,6,6,7,7,8,8,8-pentadecafluoro octyl (meth)acrylate; 3,3,4,4,5,5,6,6,7,7,8,8,8-tridecafluoro octyl (meth)acrylate; 2,2,3,3,4,4,5,5,6,6,7,7,8,8,9,9,10,10,10-nonadecafluorodecyl (meth)acrylate; 3,3,4,4,5,5,6,6,7,7,8,8,9,9,10,10,10-heptadecafluorodecyl (meth)acrylate; 2-trifluoromethyl-3,3,3-trifluoropropyl (meth)acrylate; 3-trifluoromethyl-4,4,4-trifluorobutyl (meth)acrylate; 1-methyl-2,2,3,3,3-pentafluoropropyl (meth)acrylate; 1-methyl-2,2,3,3,4,4,4-heptafluorobutyl (meth)acrylate; 2,2,3,3,4,4-hexafluorocyclobutyl (meth)acrylate; 2,2,3,3,4,4,5,5-octafluorocyclopentyl (meth)acrylate; 2,2,3,3,4,4,5,5,6,6-decafluorocyclohexyl (meth)acrylate; 2,2,3,3,4,4,5,5,6,6,7,7-dodecafluorocycloheptyl (meth)acrylate; 2,2,3,3,4,4,5,5,6,6,7,7,8,8-tetradecafluorocyclooctyl (meth)acrylate; 2-trifluoromethylcyclobutyl (meth)acrylate; 3-trifluoromethyl cyclobutyl (meth)acrylate; 2-trifluoromethyl cyclopentyl (meth)acrylate; 3-trifluoromethyl cyclopentyl (meth) acrylate; 2-trifluoromethyl cyclohexyl (meth)acrylate; 3-trifluoromethyl cyclohexyl (meth)acrylate; 4-trifluoromethyl cyclohexyl (meth)acrylate; 2-trifluoromethyl cycloheptyl (meth)acrylate; 3-trifluoromethyl cycloheptyl (meth)acrylate; and 4-trifluoromethylcycloheptyl (meth)acrylate.

The fluorinated (meth)acrylate monomer may comprise an alkylene linking group between a terminal fluoroalkyl group and a terminal (meth)acrylate group. In this embodiment, the fluorinated (meth)acrylate monomer has the formula

Rf-L-(CH$_2$)$p$-OC(O)C(R)=CH$_2$ wherein Rf is a perfluoroalkyl group as previously described, R is methyl or H, and L is a covalent bond.

In other embodiments, L is a divalent linking group that comprises other atoms such as oxygen, nitrogen, and/or sulfur. One representative linking group is —SO$_2$N(R)—, wherein R is methyl or H.

In typical embodiments, the fluorinated monomer comprises a fluoroalkyl or perfluoroalkyl group and an acrylate group. Fluorinated monomers comprising an acrylate group are often low Tg monomers; whereas fluorinated monomers comprising a methacrylate group are often high Tg monomers. For example, 2,2,2-trifluoroethyl acrylate homopolymer has a Tg of −10° C.; whereas 2,2,2-trifluoroethyl methacrylate homopolymer has a Tg of 69° C. As yet another example, hexafluoroisopropyl acrylate homopolymer has a Tg or −23° C.; whereas hexafluoroisopropyl methacrylate homopolymer has a Tg of 40° C.

The (meth)acrylate copolymer preferably comprises interpolymerized monomer units of at least one low Tg fluorinated monomer having a Tg ≤30° C. (i.e. a homopolymer of the fluorinated monomer has a Tg ≤30° C.). In typical embodiments, the fluorinated monomer has a Tg of less than 25° C., 20° C., 15° C., 10° C., 5° C., 0° C., or −5° C. In some embodiments, the fluorinated monomer has a Tg of at least −25° C. or −20° C., such as in the case of 2,2,2-trifluoroethyl acrylate. In other embodiments, the fluorinated monomer has a Tg less than −25° C. or −20° C. and typically at least −100° C., −75° C. or −50° C., such as in the case of 1H,1H,5H-octafluoropentyl acrylate.

In some embodiments, the (meth)acrylate copolymer comprises interpolymerized monomer units of two or more low Tg fluorinated monomers. Further, the (meth)acrylate copolymer can also be prepared from at least one fluorinated monomer having a Tg ≤30° C. and at least one fluorinated (e.g. methacrylate) monomer having a Tg greater than 30° C.

The inclusion of at least one low Tg fluorinated monomer in the (meth)acrylate copolymer of the conformable coating is beneficial for reducing the blocking of the conformable coating, while concurrently reducing film failures when the (dried) conformable coating is elongated.

The (meth)acrylate copolymer typically comprises at least 5, 6, 7, 8, 9 or 10 wt-% of the interpolymerized monomer units of the fluorinated monomer having a Tg <20° C. The (meth)acrylate copolymer may comprise up to 50, 45, or 40 wt-% of the interpolymerized monomer units of the fluorinated monomer. In some embodiments, the (meth)acrylate copolymer typically comprises no greater than 35, 30, 25, or 20 wt-% of the interpolymerized monomer units of the fluorinated monomer having a Tg <20° C.

The (meth)acrylate copolymer further comprises interpolymerized monomer units of a high Tg monomer, [M$^{highTg}$], having a Tg ≥50° C. (i.e. a homopolymer of the monomer has a Tg ≥50° C.). In some embodiments, the high Tg monomer has a Tg of at least 60° C., 70° C., 80° C., 90° C. or 100° C. The high Tg monomer typically has a Tg no greater than 175° C. and in some embodiments no greater than 170° C., 165° C., 160° C., 155° C. or 150° C. In some embodiments, the copolymer is tacky and the addition of a high Tg monomer raises the Tg and the modulus of the copolymer and reduces the tackiness. Suitable high Tg monomers include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

In some embodiments, the (meth)acrylate copolymer comprises interpolymerized monomer units of one or more non-acid high Tg monomers, as just described. The (meth)acrylate copolymer can be free of acid functional high Tg monomers.

In other embodiments, the (meth)acrylate copolymer comprises at least one acid functional high Tg monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

The presence of acid functional monomers in the copolymer can enhance the physical integrity and resilience by the ionic crosslinking (hydrogen bonding). Acid functional monomers can also stabilize cyanoacrylate due to the acidity of the carboxylic acid.

Due to their availability, acid functional monomers of the acid functional copolymer are generally selected from ethylenically unsaturated carboxylic acids, such as acrylic acid and methacrylic acid. When even stronger acids are desired, acidic monomers include the ethylenically unsaturated sulfonic acids and ethylenically unsaturated phosphonic acids.

The (meth)acrylate copolymer typically comprises at least 5, 10, or 15 wt-% of the interpolymerized monomer units of a high Tg monomer(s). The (meth)acrylate copolymer may comprise up to 80, 70, 60, 50 or 40 wt-% of the interpolymerized monomer units of the high Tg monomer(s). In some embodiments, the (meth)acrylate copolymer comprises no greater than 30 wt-% of the interpolymerized monomer units of high Tg monomer.

In some embodiments, the (meth)acrylate copolymer comprises interpolymerized monomer units of two or more high Tg monomers. In some embodiments, two different non-acid Tg monomers may be utilized that typically differ in Tg. For example, acid functional monomer(s) may be utilized in combination with non-acid high Tg monomer(s). In this later embodiments, the (meth)acrylate copolymer may comprises at least 0.1, 0.5, or 0.1 wt-% of acid functional monomer ranging up to 5, 6, 7, 8, 9, or 10 wt-%.

The (meth)acrylate copolymer comprises interpolymerized monomer units of a silane monomer [M$^{Silane}$]. The silane monomer has a Tg <50° C. or <40° C. and in some embodiments less than <30° C., <20° C., or <10° C.

In some embodiments, the silane monomer has the formula:

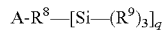

A-R$^8$—[Si—(R$^9$)$_3$]$_q$ wherein:

A is an ethylenically unsaturated polymerizable group, including vinyl, allyl, vinyloxy, allyloxy, and (meth)acryloyl, preferably (meth)acrylate;

$R^8$ is a covalent bond or a divalent (hetero)hydrocarbyl group, q is at least one, preferably greater than 1, more preferably 3;

$R^9$ is a monovalent alkyl, aryl or a trialkylsilyloxy group, q is 1, 2 or 3, preferably 1.

In one embodiment $R^8$ is a di- or polyvalent hydrocarbon bridging group of about 1 to 20 carbon atoms, including alkylene and arylene and combinations thereof, optionally including in the backbone 1 to 5 moieties selected from the group consisting of —O—, —C(O)—, —S—, —SO$_2$— and —NR$^1$— groups (and combinations thereof such as —C(O)—O—), wherein $R^1$ is hydrogen, or a $C_1$-$C_4$ alkyl group. Preferably, $R^8$ is a divalent alkylene.

Useful silane monomers include, for example, 3-(methacryloyloxy) propyltrimethylsilane, 3-acryloxypropyltrimethylsilane, 3-acryloyloxypropyltriethylsilane, 3-(methacryloyloxy)propyltriethylsilane, 3-(methacryloyloxy) propylmethyldimethylsilane, 3-(acryloyloxypropyl) methyldimethylsilane, 3-(methacryloyloxy)-propyldimethylethylsilane, 3-(methacryloyloxy) propyldiethylethylsilane, vinyldimethylethylsilane, vinylmethyldiethylsilane, vinyltriethylsilane, vinyltriisopropylsilane, vinyltrimethylsilane, vinyltriphenylsilane, vinyltri-t-butylsilane, vinyltris-isobutylsilane, vinyltriisopropenylsilane, vinyltris(2-methylethyl)silane, 3-[tris(trimethylsiloxy)silyl]propyl methacrylate, and mixtures thereof.

In other useful embodiments, the silane-functional monomer may be selected from silane functional macromers, such as those disclosed in US 2007/0054133 (Sherman et al.) and US 2013/0224373 (Jariwala et al.), incorporated herein by reference. The preparation of silane macromonomer and subsequent co-polymerization with vinyl monomer have been described in several papers by Y. Yamashita et al., Polymer J. 14, 913 (1982); ACS Polymer Preprints 25 (1), 245 (1984); Makromol. Chem. 185, 9 (1984), and in U.S. Pat. Nos. 3,786,116 and 3,842,059 (Milkovich et al.). This method of macromonomer preparation involves the anionic polymerization of hexamethylcyclotrisiloxane monomer to form living polymer of controlled molecular weight, and termination is achieved via chlorosilane compounds containing a polymerizable vinyl group. Free radical co-polymerization of the monofunctional siloxane macromonomer with vinyl monomer such as methyl methacrylate or styrene provides siloxane grafted co-polymer of well-defined structure, i.e., controlled length and number of grafted siloxane branches. Such macromers include poly(3-methacryloyloxypropyltris(trimethylsiloxy)silane (TRIS)-co-methyl methacrylate-co-isooctyl acrylate.

The (meth)acrylate copolymer typically comprises at least 5, 10, or 15 wt-% of interpolymerized monomer units of silane monomer. The (meth)acrylate copolymer may comprise up to 90, 80, 70 or 60 wt-% of the interpolymerized monomer units of silane monomer. In some embodiments, the (meth)acrylate copolymer comprises at least 40 wt-% of interpolymerized silane monomer units.

The (meth)acrylate copolymer may optionally comprise interpolymerized units of monomer(s) having a pendent crystalline group. Such monomers are described in U.S. Application Ser. No. 61/950,284, incorporated hereby reference, and can also contribute to reduced blocking of the dried coating and/or reduced failure when the dried coating is elongated. By "crystalline" it is meant that a monomer displays a crystalline melting point ≥30° C. when measured in the composition by differential scanning calorimetry (DSC) and the copolymer preferably has a $T_m$ of ≥20° C. The peak temperature of the observed endotherm is taken as the crystalline melting point. The crystalline phase includes multiple lattices in which the copolymer assumes a conformation in which there is a highly ordered registry in adjacent chemical moieties of the crystalline monomer. The packing arrangement (short order orientation) within the lattice is highly regular in both its chemical and geometric aspects. Generally, the monomer per se will have a $T_m$>30° C., however once incorporated into the copolymer, the $T_m$ may be depressed, yet the copolymer preferably exhibits a $T_m$>20° C.

Preferred crystalline polymeric materials are acrylate or methacrylate polymers derived from acrylate or methacrylate esters of non-tertiary higher alkyl alcohols. The alkyl groups of these alcohols contain at least about 18, preferably about 24-36 carbon atoms. Thus, the preferred crystalline polymeric materials of the present invention include poly (dodecyl acrylate), poly(isotridecyl acrylate), poly(n-tetradecyl acrylate), poly(n-hexadecyl acrylate), poly(n-hexadecyl methacrylate), poly(n-octadecyl acrylate), poly(behenyl acrylate), poly(eicosanyl acrylate), and mixtures thereof. Of these, poly(n-octadecyl acrylate), poly(behenyl acrylate), and mixtures or copolymers thereof are preferred. As determined by DSC, poly(octadecyl acrylate) has a melting point in the range of about 42° C. to about 49° C. with an enthalpy of fusion of about 77 Joules/gram and poly(behenyl acrylate) has a melting point in the range of about 62° C. to about 72° C. and an enthalpy of fusion of about 105 Joules/gram. These crystalline polymers are particularly preferred due to their solubility in organic solvents near and above their respective melting temperatures. This facilitates formation of a continuous crystalline component distinct from the copolymer component.

The (meth)acrylate copolymer may also optionally comprise lower Tg (meth)acrylate monomers or other free-radically polymerizable monomers such as (meth)acrylamide or vinyl monomers. Examples of such free-radically reactive monomers include, but are not limited to, tert-butyl acrylate, isobornyl acrylate, butyl methacrylate, vinyl acetate, acrylonitrile, styrene, isooctyl acrylate, n-butyl acrylate, 2-ethylhexyl acrylate, and the like. Various combinations of these monomers can be used.

The fluorinated monomer, high $T_g$ monomer, silane monomer together with the optional monomers are used in amounts sufficient such that the $T_g$ of the copolymer to ≥−20° C. or −10° C. or 0° C. The Tg is typically no greater than 50° C., 45° C., 40° C., 35° C., 30° C. or 25° C. In some embodiments, the Tg is no greater than 20° C. or 15° C. By Tg it is meant the calculated $T_g$ for specific combinations of various monomers as can be computed by application of Fox Equation: $1/T_g = \Sigma Wi/T_g i$. In this equation, $T_g$ is the glass transition temperature of the mixture, Wi is the weight fraction of component i in the mixture, and $T_g i$ is the glass transition temperature of component i, when polymerized as a homopolymer, and all glass transition temperatures are in Kelvin (K).

The resulting (meth)acrylate copolymer may be represented by the general formula: ~[$M^{fluor}$]$_v$-[$M^{silane}$]$_w$-[$M^{highTg}$]$_y$,~, which may be random or block and each subscript represents the wt-% of the monomer units, as described herein.

The weight average molecular weight of the (meth) acrylate copolymer is generally 30,000-5,000,000 g/mole. The weight average molecular weight of the copolymer is preferably greater than 50,000, 75,000 or 100,000 g/mole. In some embodiments, the weight average molecular weight of the copolymer is no greater than 1,000,000 g/mole.

The (meth)acrylate copolymer component is typically not crosslinked, at least because preparation is easier, as crosslinked polymer tends to gel and provides high viscosity solutions which provide poor, non-uniform coatings which may suffer poorer elasticity.

The (meth)acrylate copolymer may be synthesized by radical, anionic or cationic polymerization of the monomers, although synthesis by radical polymerization is preferred for ease of reaction with a greater variety of usable monomers. The initiator for the radical polymerization may be a thermal initiator which generates radicals by heat, or a photoinitiator which generates radicals by light.

Examples of thermal initiators which may be used include azo compounds such as 2,2'-azobis(2,4-dimethylvaleronitrile), 2,2'-azobisisobutyronitrile, 2,2'-azobis(2-methylbutyronitrile), 1,1'-azobis(1-cyclohexane-1-carbonylnitrile) and dimethyl-2,2'-azoisobutyrate, as well as peroxides such as benzoyl peroxide, lauroyl peroxide and t-butyl peroxypivalate. Examples of photoinitiators which may be used include benzoin ethers such as benzoin methyl ether and benzoin butyl ether, acetophenone derivatives such as 2,2-dimethoxy-2-phenylacetophenone and 2,2-diethoxyacetophenone, and acylphosphine oxide and acylphosphonate derivatives such as diphenyl-2,4,6-trimethylbenzoylphosphine oxide, isopropoxy(phenyl)-2,4,6-trimethylbenzoylphosphine oxide and dimethylpivaloylphosphonate.

A chain transfer agent may also be used during synthesis of the (meth)acrylate copolymer to adjust the polymer molecular weight. Chain transfer agents which may be used are mercapto compounds such as dodecylmercaptan and halogen compounds such as carbon tetrabromide.

The coating composition further comprises a volatile solvent. The composition has a viscosity less than 1,000 cps and a solubility parameter from 4.9-12.5 $(cal/cm^3)^{1/2}$. In one embodiment, the volatile solvent is selected from the group consisting of volatile linear and cyclic siloxanes, volatile polydimethylsiloxanes, isooctane, octane, and combinations thereof. The solvent is at least 40% wt. of the total composition. As the composition may be applied to tissue, the solvent is desirably volatile and non-stinging. In one embodiment, at least 60% wt. of the total composition is the solvent. In one embodiment, the composition further comprises an anti-blocking agent. In one embodiment, the viscosity is less than 100 cps.

In one embodiment, the composition further comprises a hemostatic agent, such as a polymerizable cyanoacrylate monomer. In other embodiments, the composition is free of polymerizable cyanoacrylate monomer. Other hemostatic agents include microfibrillar collagen, chitosan, bone wax, ostene, oxidized cellulose and thrombin.

Cyanoacrylate monomers that may be used include readily polymerizable alpha-cyanoacrylates, including alkyl cyanoacrylates, aryl cyanoacrylates, alkoxyalkyl cyanoacrylates, such as butyl cyanoacrylate and n-butyl cyanoacrylate in particular, octyl cyanoacrylate and 2-octyl cyanoacrylate in particular, ethyl cyanoacrylate, methyl cyanoacrylate, n-dodecyl cyanoacrylate, phenyl 2-cyanoacrylate, methoxyethyl 2-cyanoacrylate, and the like. The composition may be composed of one or more polymerizable cyanoacrylate monomers.

When present, the cyanoacrylate monomer is used in amounts of 1:2 to 2:1, preferably 1.5:1 to 1:1.5 relative to the amount of the copolymer. Generally, the cyanoacrylate is present in at least 5%, by weight, of the nonvolatile portion of the composition, so that the system demonstrates good hemostatic and lymphostatic performance.

When a cyanoacrylate is present, the coating composition desirably contains an effective amount of a stabilizer (i.e., an amount which provide a coating composition which exhibits substantially no gelation when stored for at least about one month at 22° C., but which, at the same time, is capable of undergoing polymerization at a practical rate). Examples of stabilizers are anionic polymerization inhibitors.

Suitable anionic polymerization inhibitors are well-known to those skilled in the art and include acidic gases such as sulfur dioxide, sulfur trioxide, nitric oxide, and hydrogen fluoride; aromatic sulfonic acids and aliphatic sulfonic acids; and organic sultones of the type disclosed in U.S. Pat. No. 3,836,377 (Delahunty), incorporated herein by reference. Also useful are boric acid or ester chelate or organic acids such as those described in U.S. Pat. No. 4,182,823 (Schoenberg), the silyl esters of sulfonic acids such as those described in U.S. Pat. No. 4,565,883 (Sieger et al.) and the bis-trialkylsilyl esters of sulfuric acid, as described in U.S. Pat. No. 4,650,826 (Waniczek et al.), incorporated herein by reference, and the corresponding silyl esters of phosphoric and phosphonic acid.

Typical rheology additives that may be added to the liquid material or formulation are fumed silica, bentonite and other clay derivatives, and the like. Fillers can also be useful in modifying the slip, hardness and blocking performance of the coating. Large particles such as glass beads can be utilized to reduce the blocking performance of the coating.

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety. Examples of suitable colorants as described in U.S. Pat. No. 5,981,621 include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

The use of florescent dyes and pigments are also beneficial by enabling the coating to be viewed under black-light. The coating would be clear and transparent under normal lighting so the site can be easily viewed and inspected for changes in the skin. As a means of ensuring the coating is intact and covering the desired area, the site can be inspected by the use of a backlight wand or flashlight which reveals the coating by its florescence. A particularly useful hydrocarbon soluble fluorescing dye is 2,5-bis(5-tert-butyl-2-benzoxazolyl) 1 thiophene.

Depending on the particular requirements of the user, the compositions can be applied by known means, such as with a spray, pump, swab, rod, sterile brush, sponge applicator or medicine dropper that may be single use or multi use items. The coating compositions are generally sealed prior to application to maintain the stability.

The coating composition, comprised of a volatile solvent and elastomer, when formed as a coating is useful for protecting or treating skin, nails, tissues, organs and mucous membranes, e.g. bleeding injuries, surgical sites, skin ulcers, cuts, abrasions, incisions, cold sores, blisters, rashes, abraded gums and other oral surfaces, hemorrhoids and abraded body areas, and other mucosal membrane incisions and wounds. The coatings may also be used as surgical glues. A coating formed from the conformable coating composition comprises a solvent borne or dispersion of an elastomer.

In addition to coating on skin or mucous membranes, the coating composition may be applied to other substrates. Useful substrates may include plastics (e.g., polypropylene, including biaxially oriented polypropylene, vinyl, polyethylene, polyester such as polyethylene terephthalate), nonwovens (e.g., papers, cloths, nonwoven scrims), metal foils, foams (e.g., polyacrylic, polyethylene, polyurethane, neoprene), and the like. In some embodiments, the coating composition may be coated on a low-surface energy substrate so that the resulting coating may be transferred to a second substrate, such as skin. Such low surface energy substrate, known as release materials include materials such as, for example, silicone, polyethylene, polycarbamate, polyacrylics, and the like. It will be understood that the optional cyanoacrylate will limit coating of other substrates.

In some embodiments, island dressings are provided comprises a coating of this disclosure on a backing layer, and an adhesive layer on the backing layer facing the coating. The adhesive layer and backing layer form a perimeter around the instant coating and hold the coating in place on an application surface. A release element is in contact with at least a portion of the edge of the pad proximate the area that the coating and release liner separate during liner removal. Details regarding the construction of such island dressing may be found in US 2011/0166492 (Burton et al.), incorporated herein by reference.

In one embodiment the conformable film described herein is provide on an elongatable, or in otherwords stretchable, substrate. In this embodiment, the conformable film may have a coating weight ranging from 1 to 30 mg/in$^2$. The conformable film does not block (e.g. rating of a 1) and has a failure no greater than 75% at 100% elongation using the test method described herein. In favored embodiments, the failure is less than 50 or 25% at 100% elongation. In one embodiment, film formed from the dried coating has a thickness of less than 1 mm. In one embodiment, the film has an elongation of at least 50%. In typical embodiments, the film has low tack, low drag, and low blocking (i.e. a rating of 1 according to the test methods described in the examples.

Examples

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Raw materials utilized in the sample preparation are shown in Table 1.

TABLE 1

| Component | Description | Supplier |
|---|---|---|
| TRIS | 3-[Tris(trimethylsiloxy)silyl]propyl methacrylate (Tg = −3° C.) | Alfa Aesar (Ward Hill, MA) |
| t-BMA | tert-Butyl Methacrylate (Tg = 118° C.) | TCI (Portland, OR) |
| n-BMA | n-Butyl Methacrylate | TCI (Portland, OR) |
| IOA | Isooctyl Acrylate (Tg = −10° C.) | 3M (St. Paul, MN) |

TABLE 1-continued

| Component | Description | Supplier |
|---|---|---|
| SMA | Stearyl Methacrylate (Tg = 38° C.) | TCI (Portland, OR) |
| TFA | 2,2,2-Trifluoroethyl acrylate (Tg = −10° C.) | SynQuest Lab. (Alachua, FL) |
| OFA | 1H,1H,5H-Octafluoropentyl acrylate (Tg = −35° C.) | SynQuest Lab. (Alachua, FL) |
| HFIPMA | Hexafluoroisopropyl methacrylate (Tg = 40° C.) | SynQuest Lab. (Alachua, FL) |
| AA | Acrylic Acid (Tg = 105° C.) | Alfa Aesar (Ward Hill, MA) |
| MMA | Methyl methacrylate (Tg = 110° C.) | TCI (Portland, OR, USA) |
| Isooctane | 2,2,4-Trimethylpentane | Alfa Aesar (Ward Hill, MA) |
| HMDS | Hexamethyldisiloxane | Alfa Aesar (Ward Hill, MA) |
| Vazo ™ 67 | 2,2'-Azobis(2-methylbutyronitrile) | Dupont (Wilmington, DE) |
| OCA | Octyl cyanoacrylate | Cyberbond (Batavia, IL) |

Test Methods

Appearance—

Solution appearance was assessed in a clear glass vial and rated for clarity. Solutions were rated as either clear, very slight haze (v slt haze), slight haze (slt haze), or hazy. All the formulation were clear unless noted otherwise.

Viscosity—

Viscosity was rated with the solution in a glass vial. The vial was tipped back and forth and the rate of solution flow was rated on a relative scale with low viscosity similar to water rated as 1 and a nonflowing gel rated as 5. All the formulations had a viscosity rating of 1 unless noted otherwise.

Tack—

Several drops of each formulation were spread across a 2.54 cm×5.08 cm CHG gel pad (for example, 3M Tegaderm™ CHG Dressing, catalogue #1657, 3M Company, St. Paul, Minn.). The formulation was spread to a thin film and was allowed to dry for at least 15 minutes at room temperature. Tack is a sensory evaluation conducted by lightly touching the cured coatings with a finger. The coatings were rated from 1 (no tack) to 5 (high tack). All the formulations had a tack rating of 1 unless noted otherwise.

Drag—

Several drops of each formulation were spread across a 2.54 cm×5.08 cm CHG gel pad. The formulation was spread to a thin film and was allowed to dry for at least 15 minutes at room temperature. Drag is a sensory evaluation conducted by lightly stroking the cured coatings with a finger. The coatings were rated from 1 (similar frictional force of skin) to 5 (high frictional force). All the formulations had a drag rating of 1 unless noted otherwise.

Blocking—

Several drops of each formulation were spread across a 2.54 cm×5.08 cm CHG gel pad. The formulation was spread to a thin film and was allowed to dry for at least 15 minutes at room temperature. Blocking is a sensory evaluation conducted by folding the gel pad over on itself and holding it together with light finger pressure (about 400 g of force over an area of 4 cm$^2$) for 1 minute. The amount of blocking was rated from 1 (no film-film adhesion) to 5 (high, required pulling to separate both sides). All the formulations had a blocking rating of 1 unless noted otherwise.

% Failure at 100% or 200% Elongation—

Several drops of each formulation were spread across a 2.54 cm×5.08 cm CHG gel pad. The formulation was spread to a thin film and was allowed to dry for at least 15 minutes at room temperature. After drying, the thin film formed from the dried coating composition had a thickness of about 5-10 microns. The CHG gel pads were then stretched to 100% or 200% of their initial length and placed on a flat surface so that they remained in their stretched position. A paper kimwipe (Kimberly Clark, Irving, Tex.) was placed over the stretched surface and several drops of common bleach are placed on top until the entire surface is wet of the coated gel. The kimwipe was removed after 1 minute. If the coating had fractured, the NaOCl in the bleach reacted with the CHG in the gel pad to form a brown color. The amount of brown coloration was reported as a percent failure. A percent failure of 50-75% is considered good (a substantial improvement), a percent failure of less than 50% better, and less than 25% best.

Comparative Copolymer Synthesis

Comparative co-polymers were prepared by bottle solution polymerization in 50 gm amounts at 25% monomer concentration with an initiator charge of 2% by wt of monomer with 2,2 azobis(2-methylbutanenitrile) utilizing 75 wt-% of ethyl acetate. Prior to polymerization, all solutions were nitrogen purged for at least 5 minutes to remove oxygen in the system. Polymerizations were conducted at 60° C. for 24 hours and were finished by lowering the reaction temperature to room temp. The copolymer was then diluted to approximately 5% solids with isopropanol. Water was slowly added to induce precipitation. The solid copolymer was isolated and dried at 60° C. for 48 hours.

Comparative liquid bandage formulations were prepared by dissolving 8% (by weight) of the comparative copolymer in HDMS with and without 8% OCA.

The wt-% solids of each of the monomers in the formulation (after evaporation of the volatile solvent), and test results are listed in the following Table 1:

TABLE 1

Comparative Liquid Bandage Formulations

| | HFIP MA | n-BMA | IOA | MMA | TRIS | OCA | Block-ing | 100% Elong. % Failure | 200% Elong. % Failure |
|---|---|---|---|---|---|---|---|---|---|
| C-1 | 10.4 | 0 | 7.2 | 35.2 | 48 | 0 | 3 | 98 | 100 |
| C-2 | 10.4 | 0 | 7.2 | 35.2 | 48 | 2.4 | 2 | 95 | 95 |
| C-3 | 10.4 | 0 | 0 | 8.8 | 80.8 | 2.4 | 3 | 85 | 95 |
| C-4 | 10.4 | 8.8 | 0 | 0 | 80.8 | 2.4 | 5 | 90 | 70 |

Copolymer Synthesis
Copolymer P-1 though P-26

P-1 was prepared by adding 2.16 g (4.8% w/w) TFA, 0.49 g (1.1% w/w) SMA, 3.97 g (7.6% w/w) MMA, 7.43 g (16.5%) TRIS, 31.5 g (70%) HMDS, and Vazo™ 67 (0.3 wt % total solids) into an amber, pint bottle. The solution was de-aerated with a nitrogen purge for 10 minutes at room temperature. The bottle capped, placed in water bath at 60° C., and mixed for 24-48 hours. The co-polymer was then diluted to approximately 5% solids with isopropanol. Water was slowly added to induce precipitation of the polymer. The solid polymer was isolated and dried at 60° C. for 48 hours.

Copolymers P-2 through P-16 were made in the same manner as described for P-1. The wt-% of each of the monomers in the copolymer are listed in Table 2.

TABLE 2

Copolymer Formulations Containing TFA

| Co-Polymer | TFA (wt-%) | TRIS (wt-%) | SMA (wt-%) | MMA (wt-%) | t-BMA (wt-%) |
|---|---|---|---|---|---|
| P-1 | 16.0 | 55.0 | 3.7 | 25.3 | 0 |
| P-2 | 23.4 | 44.6 | 0 | 0 | 32.0 |
| P-3 | 16.0 | 54.9 | 0 | 0 | 29.1 |
| P-4 | 28.6 | 44.0 | 0 | 0 | 27.4 |
| P-5 | 28.0 | 40 | 0 | 0 | 32.0 |
| P-6 | 20.6 | 52.6 | 0 | 0 | 26.9 |
| P-7 | 16.0 | 52.0 | 0 | 0 | 32.0 |
| P-8 | 27.4 | 50.6 | 0 | 0 | 22.0 |
| P-9 | 24.6 | 48.0 | 0 | 0 | 27.4 |
| P-10 | 32.0 | 40 | 0 | 0 | 28.0 |
| P-11 | 32.0 | 46.0 | 0 | 0 | 22.0 |

A second group of copolymers were prepared with two fluorinated acrylates, TFA and OFA, in a solvent of HDMS (about 65 wt-% solvent). The wt-% of each of the monomers in the copolymer are listed in Table 3.

TABLE 3

Copolymer Formulations Containing TFA and/or OFA

| Co-Polymer | TFA (wt-%) | OFA (wt-%) | SMA (wt-%) | t-BMA (wt-%) | TRIS (wt-%) | AA (wt-%) |
|---|---|---|---|---|---|---|
| P-12 | 0 | 34.9 | 0 | 18.9 | 46.0 | 0 |
| P-13 | 14.9 | 10 | 10.9 | 18.0 | 46.0 | 0 |
| P-14 | 8.6 | 26.3 | 0 | 35.1 | 30 | 0 |
| P-15 | 0 | 10 | 20 | 24.3 | 45.7 | 0 |
| P-16 | 14.9 | 10 | 8.0 | 21.4 | 45.7 | 1.1 |
| P-17 | 4.0 | 22.3 | 5.1 | 23.7 | 44.9 | 1.1 |
| P-18 | 14.9 | 10 | 10.9 | 18.0 | 46.0 | 2.0 |

Liquid Bandage Formulations

To make E-1, P-1 was diluted to approximately 30% solids with HMDS. In a glass vial, 0.80 g of the diluted P-1 and 1.96 g HMDS were mixed for about 20 seconds until homogeneous. If necessary, the solution was heated to 60° C. and vortexed until homogeneous.

The solution was then returned to room temperature and 0.24 gms of OCA was added and the solution vortexed until uniform. The final composition was approximately 8% (w/w) P-1 solids (27% w/w of the diluted P-1), 8% (w/w) OCA, and 65% (w/w) HMDS.

E-2 through E-26 were prepared as described in E-1. Each formulation was prepared with the copolymer of the same number.

The liquid bandage formulations were evaluated according to the test methods previously described. The test results are set forth in the following Table 4 and 5.

TABLE 4

Test Results of Copolymer Formulations Containing TFA

| | Appearance | | % Failure | |
|---|---|---|---|---|
| Example | Before OCA add | After OCA add | 100% Elongation | 200% Elongation |
| E-1 | clear | clear | 20 | 80 |
| E-2 | clear | v slt hazy | 75 | 80 |
| E-3 | clear | v slt hazy | 55 | 90 |
| E-4 | clear | v slt hazy | 25 | 60 |
| E-5 | clear | v slt hazy | 35 | 70 |
| E-6 | clear | v slt hazy | 50 | 50 |
| E-7 | clear | v slt hazy | 50 | 90 |
| E-8 | clear | v slt hazy | 50 | 70 |

TABLE 4

Test Results of Copolymer Formulations Containing TFA and/or OFA

| | Appearance | | | % Failure | |
|---|---|---|---|---|---|
| Example | Before OCA add | After OCA add | Viscosity | 100% Elongation | 200% Elongation |
| E-9 | clear | v slt hazy | | 60 | 85 |
| E-10 | clear | v slt hazy | | 55 | 90 |
| E-11 | clear | v slt hazy | | 20 | 80 |
| E-12 | clear | clear | 1 | 50 | 95 |
| E-13 | clear | clear | 1 | 50 | 90 |
| E-14 | hazy | clear | 1.5 | 45 | 95 |
| E-15 | hazy | clear | 1 | 60 | 85 |
| E-16 | NT [b] | clear | 1 | 40 | 55 |
| E-17 | NT | clear | 1 | 40 | 80 |
| E-18 | NT | clear | 1 | 75 | 90 |

What is claimed is:

1. A conformable coating composition comprising:
a (meth)acrylate copolymer comprising interpolymerized monomer units of 2,2,2-trifluoroethyl acrylate in an amount ranging from 10-40 wt-% based on the weight of the (meth)acrylate copolymer; and
a volatile solvent having a solubility parameter from 4.9-12.5 (cal/cm³)^{1/2}, wherein the volatile solvent is selected from the group consisting of volatile linear and cyclic siloxanes, volatile polydimethylsiloxanes, isooctane, octane, and combinations thereof, and
wherein the conformable coating composition is free of polymerizable cyanoacrylate monomer.

2. The conformable coating composition of claim 1, the (meth)acrylate copolymer further comprising interpolymerized monomer units of a high Tg monomer in an amount ranging from 15 to 40 wt-% based on the weight of the (meth)acrylate copolymer, wherein the high Tg monomer has a Tg ≥50° C.

3. The conformable coating composition of claim 2, the high Tg monomer comprising an acid-functional group.

4. The conformable coating composition of claim 1, the (meth)acrylate copolymer further comprising interpolymerized monomer units of a silane monomer, wherein the silane monomer has a Tg <10° C.

5. The conformable coating composition of claim 4, the interpolymerized monomer units of the silane monomer being present in an amount ranging from 15 to 60 wt-% based on the weight of the (meth)acrylate copolymer.

6. The conformable coating composition of claim 4, wherein the silane monomer is represented by the formula:

$$A\text{-}R^8\text{—}[Si\text{—}(R^9)_3]_q,$$

wherein:
A is an ethylenically unsaturated polymerizable group selected from vinyl, allyl, vinyloxy, allyloxy, and (meth)acryloyl;
$R^8$ is a covalent bond or a divalent (hetero)hydrocarbyl group;
each $R^9$ is independently selected from a monovalent alkyl, aryl, alkoxy, and trialkylsilyloxy group; and
q is at least one.

7. The conformable coating composition of claim 1, wherein the composition comprises at least 40 wt. % of the volatile solvent.

8. A conformable film comprising the coating composition of claim 1.

9. A multilayer article comprising:
the conformable film of claim 8; and
a substrate,
wherein the conformable film forms a layer on the substrate.

* * * * *